United States Patent [19]

Gadow et al.

[11] Patent Number: 4,645,646

[45] Date of Patent: Feb. 24, 1987

[54] LUMINESCENCE IMMUNOASSAY FOR HAPTENS AND CHEMILUMINESCENCE LABELLED HAPTEN CONJUGATES

[75] Inventors: André Gadow, Lubeck; W. Graham Wood, Gross-Grönau, both of Fed. Rep. of Germany

[73] Assignee: Henning Berlin GmbH Chemie-und Pharmawerk, Berlin, Fed. Rep. of Germany

[21] Appl. No.: 635,194

[22] Filed: Jul. 27, 1984

[30] Foreign Application Priority Data

Jul. 29, 1983 [DE] Fed. Rep. of Germany ....... 3327327

[51] Int. Cl.$^4$ ................... B65D 69/00; G01N 33/545
[52] U.S. Cl. ..................................... 422/61; 436/531; 436/532; 436/533; 436/534; 436/535; 436/536; 436/537; 436/808
[58] Field of Search ............................. 422/56–61; 436/531–537

[56] References Cited

U.S. PATENT DOCUMENTS 4,000,252 12/1976 Kosak ................................ 424/1.1
4,362,697 12/1982 Tabb et al. ............................ 422/56
4,380,580 4/1983 Boguslaski et al. ................. 436/500

OTHER PUBLICATIONS

Pazzagli et al., Abst: XI Int./IV Eur. Cong. Clin. Chem., Vienna, from J. Clin. Chem. Clin. Biochem., 19 (1981) 798–9.
Campbell et al., Biochem. J. (1983) 216:185–94.
Patel et al., Analyt. Biochem. 129 (1983) 162–9.
Kohen et al., Febs Letters, 104 (1979) 201–5.
Kohen et al., Steroids, 36 (1980) 421–37.
Messeri et al, Clin. Chem. (1984) 30:653–7.

*Primary Examiner*—Christine M. Nucker
*Attorney, Agent, or Firm*—Wegner & Bretschneider

[57] ABSTRACT

Luminescence immunoassays for haptens can be improved and made more sensitive by using a luminescence labelled hapten conjugate which contains as the linkage group a chain-like polymer having repeating functional groups having bound thereto per mole both a plurality of moles of groups capable of luminescence and a plurality of moles of hapten. The antibody used is preferably one which is prepared by the use of another chain-like polymer having bound thereto the hapten by a different chemical reaction.

12 Claims, No Drawings

LUMINESCENCE IMMUNOASSAY FOR HAPTENS AND CHEMILUMINESCENCE LABELLED HAPTEN CONJUGATES

It is an object of the present invention to provide a luminescence immunoassay for haptens, the chemiluminescence labelled hapten conjugates contained therein and a process of preparing the same.

Luminescence immunoassays for haptens consist of (A) an antibody which is specific for the particular hapten and (B) a chemiluminescence labelled hapten conjugate. This hapten conjugate generally contains a group which is capable of chemiluminescence, a linkage group and a hapten. The linkage group may, in the simplest case, be replaced by a direct chemical bond, but it is usual to achieve a certain spatial distance by a linkage group. Therefore, the linkage group is in most cases referred to as "spacer." It has been found that, by a direct coupling of haptens with a group which is capable of chemiluminescence, the properties of both groups were changed such that the sensitivity and specificity of the tests were reduced. On the one hand, the chemiluminescent properties and, on the other hand, the specificity of the hapten with respect to its antibody were changed.

Typical chemiluminescence labelled conjugates and luminescence immunoassays containing them are, for example, known from German published application DE-OS 29 21 781. According to this publication, the linkage group R (also referred to therein as bridge group) should have a maximum of 1 to 50 and preferably 1 to 10 carbon atoms or heteroatoms so that the molecular weight of this group does not exceed 1000 and is preferably less than 200. While the luminescence immunoassays described therein have the advantage, as compared with radioimmunoassays, of not having to work with radioactive substances which have only a limited shelf life and may be used to a limited extent because of the corresponding protective regulations, they do not, on the other hand, reach by far the sensitivity or reproducibility known for radioimmunoassays.

From published German application DE-OS 29 13 549 there are known chemically induced fluorescence immunotests in which the antiligand is linked specifically to the epitopic center of the ligand and there is provided as tracer a light-emitting reciprocal pair which consist of a chemiluminescence source and a quencher which is capable of extinguishing without collisions the light emitted by the chemiluminescence source. This results in the formation of conjugates with chemiluminescence labelling and conjugates having a quencher labelling and in the binding of these conjugates to constituents of the immunological pair. The principle described therein is based on the finding that if a dye is present within a limited distance from a chemiluminescent compound or group in the excited state, the chemiluminescent compound or group is able to transfer its energy to the quencher without direct contact and without emission of radiation. The quencher is then able to emit the radiation at a higher wave length than the chemiluminescent compound or group and may lose the energy by radiationless disintegration. It is possible on principle in this case to couple to higher molecular weight ligands a plurality of moles to chemiluminescent substance or quencher. It is mentioned in the specification that it is possible on principle to link also a plurality of tracers to the formation of what is known as polyligand-analogous tracers. However, particular advantages of such systems are not mentioned. A disadvantage resides in the fact that the analogous pair must contain the quencher at comparable distances in order to be correspondingly active. When using relatively small haptens, attention is to be directed to the peculiarity that these lead frequently to a substantially reduced chemiluminescence without an express quencher being additionally linked to the receptor. This reciprocal effect between the hapten and chemiluminescent group was previously observed in a plurality of cases and resulted in a reduced sensitivity and specificity of the tests so that use is preferably made in such cases of a "spacer."

It is an object of the present invention to improve luminescence immunoassays for haptens and to make them comparable with the radioimmunoassays with respect to handling, sensitivity and reproducibility. At the same time, it is aspired to make the individual constituents of this immunoassay producible in a simple and reproducible manner and at a larger scale. This object was surprisingly accomplished by using a chemiluminescence labelled hapten conjugate which, between the group capable of chemiluminescence and the hapten, has a linkage group which is a chain-like polymer having recurring functional groups to 1 mole of which there has been bonded a plurality of moles of groups capable of luminescence and also a plurality of moles of hapten.

This result was not predictable because, according to the status of the art, the linkage groups should be kept as small as possible and only one group capable of chemiluminescence should also be linked to a hapten. Surprisingly, it has been found that the sensitivity and reproducibility of a chemiluminescence immunoassay for haptens can be substantially improved if, instead, a plurality of moles of the group capable of chemiluminescence are linked with a plurality of moles of the hapten in such a manner that they are linked at a sufficient distance to a chain-like polymer.

As a further component for the luminescence immunoassay according to the invention, an antibody which is specific for the hapten is used and which is preferably recovered by the use of another chain-like polymer having bound thereto a plurality of moles of hapten by a different chemical reaction. The antibodies thus obtained are highly specific with respect to the hapten in a free form and also in the linked form to a chain-like polymer. On the other hand, these antibodies do not exhibit a specific linking capacity for other chain-like polymers to which groups were coupled with a different chemical reaction.

In particular, peptides, glycoproteins, glycolipids or carbohydrates may be used as chain-like polymers having repeating functional groups. Typical examples of such polymers include polysaccharides such as dextrans, pectins, lectins and natural gums, peptides such as p-Lys, p-Lys-Tyr, p-Glu-Tyr, proteins such as serum albumin and globulins, glycoproteins such as transferrin, thyroglobulin, orosomucoid, etc. The polymers must have a sufficient number of repeating functional reactive groups capable of chemiluminescence and the haptens may be coupled to the polymer by means of usual and known methods.

Examples of such coupling reactants include for the direct coupling glutardialdehyde, cyanogen bromide, hydrazines, bisepoxiranes, divinyl sulfones, epichlorohydrins, benzoquinones, periodates, trichloro-s-triazines, isothiocyanates, arylamines and phenylhydrazines. Examples of the resultant linkage types include Michael adducts and Schiff bases, cyanate esters, triazinyls, ethers, imidocarbonates, amides, mixed anhydrides, alkylamines, and esters. Suitable reagents for the indirect coupling include, for example, EEDQ (N-ethoxy-carbonyl-2-ethoxy-1,2-dihydroquinoline) carbodiimides such as dicyclohexylcarbodiimide, 1-cyclohexyl-3-(2-morpholinyl-(4)-ethyl) carbodiimidemethyl-p-toluene sulfonate, 1-ethyl-3-(3-dimethylaminopropyl) carbodiimide hydrochloride and N-hydroxysuccinimides. Suitable are also heterobifunctional reagents such as MBS (m-maleimidobenzoyl-N-hydroxysuccinimide ester) and others.

Suitable groups capable of chemiluminescence include, on principle, all of the substances which are known for this purpose and which, for example, are summarized in detail in German published patent application DE-OS 29 21 781. Further suitable groups include certain acridinium esters, oxalate esters as well as the fluorescein isothiocyanate described in DE-OS 31 32 491.

Suitable haptens include all of the analytically interestingly organic substances which develop an immunochemical reaction in a guest animal when injected in the form of an immunogenic conjugate from the hapten and a supporting molecule. Typical haptens and the production of antibodies which are specific against them are described in DE-OS 29 21 781, pages 45 to 53.

It has been found that a suitable group which is capable of chemiluminescence is luminol which, in diazotated form as diazoluminol, can be bound to a polymer having groups which are suitable for diazo coupling. The haptens are preferably bound to the polymer through a carbodiimide reaction. For example, the glycoprotein transferrin has been found to be outstandingly suitable as a polymer.

The antibody against the particular hapten is preferably produced by coupling this hapten with another carbodiimide to a different polymer, for example, serum albumins and herewith treating the animal selected for the preparation of antibodies.

It has been found that antibodies of this kind are highly specific for both the pure hapten and for the chemiluminescence labelled hapten conjugate. On the other hand, non-specific effects and cross-reactions are avoided in this case.

The quantity of the groups capable of chemiluminescence as well as the quantity of the hapten which is bound to the polymer used in the linkage group should be generally at least 10, which results in a molar ratio of the linkage group to the group capable of luminescence to hapten of at least 1:10:10.

For the luminescence immunoassays according to the invention, the antibody which is specific for the hapten is preferably bound to a solid support. Intense preliminary studies by applicants revealed that particularly suitable solid supporting materials are polystyrene balls which have been activated with a synthetic polypeptide such as p-Phe-Lys and glutardialdehyde. However, other solid supporting materials are also suitable on principle provided that the antibody can be bound thereto in a reproducible and uniform manner without a considerable detraction from its specific reactivity.

The measurement of the chemiluminescence of luminol and luminol derivatives may be effected on balls of this kind in a very simple manner in a measuring cuvette to which hydrogen peroxide and peroxidase in an alkaline medium are added. The light reaction thereby occurring may be measured in known devices such as, for example, the Luminometer LKB 1251 of the firm LKB. The handling, sensitivity and precision of luminescence immunoassays of this kind for haptens has been found to be completely comparable with that of corresponding radioimmunoassays. Moreover, these luminescence immunoassays according to the invention are also suitable for automation and may, therefore, be also used in fully automatic devices.

In the examples which follow, chemiluminescence labelled hapten conjugates according to the invention and luminescence immunoassays for haptens prepared by means of them are described in greater detail. In these examples, the specifically selected groups capable of chemiluminescence, linkage groups and haptens are not intended to be a restriction of the invention.

EXAMPLE 1

(i) Preparation of a chemiluminescence labelled hapten conjugate such as, for example, (triiodothyronine($T_3$))-transferrin-(diazoluminol).

(a) Preparation of a transferrin-$T_3$ conjugate by means of carbodiimide coupling:

44 mg of transferrin (human, Behring-Werke, molecular weight 88,000) (0.5 $\mu$M) are dissolved in 2 ml of bidistilled water. After rapid addition of 42.9 mg (100 $\mu$M) of MCDI (1-cyclohexyl-3-(2-morpholinyl-(4)-ethyl)carbodiimide-methyl-p-toluene-sulfonate) (Merck, molecular weight 429) dissolved in 500 $\mu$l of bidistilled water, the pH is adjusted to 6 with stirring by dropwise addition of 0.01N hydrochloric acid. 17 mg of triiodothyronine ($T_3$) (molecular weight 673, Sigma) are suspended in 1 ml of bidistilled water and, with dropwise addition of a 0.5N NaOH solution, stirred to complete dissolution. This solution is dropwise added with stirring to the above-mentioned solution while maintaining the pH at 6 by adding 0.05N hydrochloric acid. Thereafter, further reaction is allowed for 2 h at room temperature and for 24 h at 3° C. The solution is centrifuged. The transferrin-$T_3$ conjugate in the supernatant is separated by gel filtration over Sephadex G-25 (Pharmacia) or Ultrogel A 6 (LKB). 10 $\mu$M/l of phosphate pH 7-8 with 0.15 M/l of sodium chloride is used as the elution buffer. The individual fractions are tested (a) photometrically for protein content and (b) for $T_3$-immunoreactivity. Those fractions which contain protein and are immunoreactive as well are combined. A substitution ratio of 14 moles of $T_3$ per mole of transferrin was calculated from the measured values. The conjugate may be freeze-dried or stored in the frozen state.

(b) Coupling of diazoluminol to the transferrin-$T_3$ conjugate.

(i) Diazotization of luminol:

0.2 mM of luminol (25.44 mg) (5-amino-2,3-dihydro-1,4-phthalazinedione, Ega-Chemie) are suspended in 5 ml of 1M/l of hydrochloric acid and with uniform stirring cooled to 0° C. in an ice bath. 1.5 mM of potassium nitrite (128 mg) are dissolved in 1 ml of water and cooled to 0° C. in an ice bath. The cold potassium nitrite solution is now added dropwise to the luminol suspension until the yellow-orange solution has been formed. Excess nitrous acid is removed by adding a urea solution. The resultant diazoluminol solution may be directly used. In the frozen state, it is stable for about one week.

Diazo coupling of the diazoluminol to the transferrin-$T_3$ conjugate:

20 mg of freeze-dried transferrin-$T_3$ conjugate are dissolved in 3 ml of water. The pH is adjusted to 9-9.5 by means of a 0.1M sodium carbonate solution. The diazoluminol solution is added dropwise at 0° C. with stirring until the ratio is 100M of diazoluminol per M of transferrin-$T_3$ conjugate. In doing so, the pH is maintained at 9 by addition of further sodium carbonate solution. The final reaction mixture is left for 24 h at 3° C. The transferrin-$T_3$ diazoluminol conjugate thus obtained is purified by gel filtration in the same manner as the transferrin-$T_3$ conjugate. The individual fractions are tested
(1) with a photometer at 280 nm,
(2) for $T_3$-immunoreactivity,
(3) for diazoluminol luminescence reaction in the LKB and
(4) for specific binding to $T_3$ antibodies and non-specific binding properties.

The fractions having a measurable protein content, a specific binding to $T_3$ antibodies, but without marked non-specific binding properties are combined. The measured values result in a substitution ratio of transferrin:$T_3$:diazoluminol of 1:14:20. The conjugate having been obtained in this manner may be both freeze-dried or stored in frozen state.

(ii) Use of the chemiluminescence labelled hapten conjugate in a luminescence immunoassay for a hapten (transferrin-$T_3$ diazoluminol in a $T_3$ chemiluminescence assay).

(a) Immobilization of antibodies on a solid supporting material ($T_3$ antibodies on polystyrene balls).

Polystyrene balls of 6.4 mm coated with a synthetic polypeptide (p-Phe-Lys, molecular weight 30,000) are activated with a 0.5% aqueous solution of pentane-1,5-dial. The resultant balls are mixed at pH 7.5-8.5 in a 0.05M/l phosphate buffer with a purified $T_3$ antibody. The $T_3$ antibody was raised in rabbit by using a $T_3$ bovine serum albumin conjugate as immunogen, prepared with 1-ethyl-3-(dimethyl-aminopropyl) carbodiimide (EDAC). The Schiff bases formed were subsequently reduced in some cases with sodium borohydride, but a substantial difference in the stability was not observed. The remaining active groups were saturated with bovine serum albumin. The saturation was completed in most cases only after several days, monitored by measuring the non-specific binding. The repeatedly washed balls were dried in a stream of air or stored in a 0.05-molar tris/hydrochloric acid buffer with the addition of bovine serum albumin. For reconstitution before use, the dried balls were placed into the same buffer for one hour.

(b) Measurement of chemiluminescence

The oxidation system used was a mixture of microperoxidase (Microperoxidase MP11-Sigma) 5 $\mu M/l$, $H_2O_2$ (0.5%) and 0.8M/l of NaOH. The buffer used was a 0.05-molar phosphate buffer of pH 7 having added thereto 0.1M of sodium chloride as well as 4 g/l of bovine serum albumin and 0.014M/l of $NaN_3$. The microperoxidase and the buffer were mixed shortly before the measurement. The final reaction solution had a pH of 13. This results in a slowing-down of the chemiluminescence kinetics, however, with an enhancement in precision. The measurement was effected after the start of the reaction by addition of $H_2O_2$ while measuring the light emission as integral during a period of 20 to 30 seconds.

(c) Performing the $T_3$ luminescence immunoassay

In each case, a 100 $\mu l$ of serum sample or standard with 200 $\mu l$ of incubation buffer (0.1M/l of tris-HCl of pH 7.4, 0.02M/l of KCl, 0.2% of bovine serum albumin) as well as 75 mg/100 ml of ANS (8-anilino-1-naphthalino-sulfonic acid) were incubated with the polystyrene balls coated with antibodies for 2 h at room temperature. Next, 50 $\mu l$ of a 1:100 dilution of the $T_3$-transferrin-diazoluminol conjugate were added, the mixture was shortly shaken and then incubated for another hour at room temperature. Washing was effected twice with the incubation buffer and once with a 0.9% sodium chloride solution. The balls are transferred into the measuring cuvettes and then the chemiluminescence was measured as described above.

Typical measuring values are summarized in Table 1. Thus, the lower limit of detection is at about 0.25 ng of $T_3$/ml.

TABLE 1

$T_3$/Luminescence assay $T_3$/RIA Chemiluminescence
(Integration time = 20 seconds)

| ng of $T_3$/ml | mV − s | MV* | B/BO × 100 in % | CPM (a) (b) | MV* | B/BO (%) |
|---|---|---|---|---|---|---|
| 0 | 415 429 | 422 | 100 | 15686 15151 | 15418 | 100 |
| 0.25 | 378 398 | 388 | 92 | 13937 13605 | 13771 | 89.3 |
| 0.50 | 324 331 | 327 | 78 | 12012 12195 | 12103 | 78.5 |
| 1 | 280 270 | 275 | 65 | 9828 9876 | 9852 | 63.9 |
| 2 | 199 210 | 204 | 48 | 7168 7194 | 7181 | 46.6 |
| 4 | 132 112 | 122 | 29 | 4981 5127 | 5054 | 32.8 |
| 8 | 66 52 | 59 | 14 | 2915 2967 | 2941 | 19.1 |

*mean value

In the following Table 2, the measured values determined according to the invention are summarized and compared with those of a radioimmunoassay.

TABLE 2

Correlation between measuring values obtained by the chemiluminescenceassay and a radioimmunoassay using three control sera for $T_3$.

| | $T_3$/RIA ng/ml | $T_3$/luminescence assay ng/ml |
|---|---|---|
| Serum I | 0.34 ± 0.2 | 0.31 ± 0.1* |
| Serum II | 1.2 ± 0.4 | 0.97 ± 0.4 |
| Serum III | 3.4 ± 1 | 2.97 ± 1.2 |

(Number of the samples measured in each case n = 20)
*represents the ±3 s.d. range.

EXAMPLE 2

In a manner analogous to that described in Example 1, a protein conjugate was prepared as follows: 385 mg of swine thyroglobulin having about 80 $\mu m$ of lysine residues were reacted with 1155 mg of succinic acid anhydride (11.6 mM). To this end, the thyroglobulin was dissolved in 25 ml of water while stirring and the pH adjusted to 7 by means of 1N NaOH. The succinic acid anhydride was added in small portions while maintaining a pH between 7 and 8 by addition of 1N NaOH. After stirring for 1 h at room temperature, the pH was adjusted to about 2.5 using 1N hydrochloric acid. A thick precipitate was formed. This suspension was transferred into an Amicon cell, concentrated to 30 ml and repeatedly suspended with 50 ml of water and again concentrated. After six washing procedures, the pH was 5. The content of the cell was subdivided in portions, frozen and freeze-dried.

A solution of 150 mg of this product in 30 ml of water was prepared and, while simultaneously adding 80 mg of water mixed with 38 mg of L-$T_4$ ethyl ester in 2 ml of methanol. The pH was adjusted to 4 by means of 1N hydrochloric acid. After 30 minutes, 80 mg of MCDI were again added. After 20 hours of stirring at room temperature, the suspension was transferred into dialyzing tubings and dialyzed for 3 days while changing the water twice daily. The dialyzing tubings were emptied and the suspension was centrifuged. The clear supernatant was subdivided into portions of 4 to 5 ml, frozen and freeze-dried. The precipitate was dissolved in ammonia or ammonium acetate and thereafter also subdivided into portions, frozen and freeze-dried. The further processing and coupling with diazoluminol was effected in a manner analogous to that described in Example 1 thereby forming a $T_4$-luminescence immunoassay.

What is claimed is:

1. A test kit for hapten luminescence immunoassay consisting of as a merchantile unit
   (A) an antibody specific to a hapten,
   (B) a chemiluminescence labelled hapten conjugate including
      (a) a plurality of groups displaying chemiluminescence,
      (b) a linkage group, and
      (c) a plurality of haptens, said linkage groups (b) being a chain-like polymer having repeating functional units and having bound thereto said plurality of groups displaying chemiluminescence (a) and said plurality of haptens (c), and
   (C) directions for carrying out said hapten luminescence immunoassy.

2. A composition according to claim 1, wherein the antibody (A) was prepared using as the immunogen a hapten bound to a linkage group other than linkage group (b).

3. A test kit according to claim 1, wherein the linkage group (b) is a peptide, a glycoprotein, a glycolipid or a carbohydrate.

4. A test kit according to claim 1, wherein the molar ratio of the linkage group (b) to the group (a) capable of chemiluminescence to the hapten (c) is at least 1:10:10.

5. A test kit according to claim 3, wherein the molar ratio of the linkage group (b) to the group (a) capable of chemiluminescence to the hapten (c) is at least 1:10:10.

6. A test kit according to claim 1, wherein the antibody (A) which is specific to the hapten is present bound to a solid supporting material.

7. A test kit according to claim 5, wherein the antibody (A) which is specific to the hapten is present bound to a solid supporting material.

8. A chemiluminescence-labelled hapten conjugate comprising
   (a) a plurality of groups displaying chemiluminescence,
   (b) a linkage group, and
   (c) a plurality of haptens, said linkage group (b) being a chain-like polymer having repeating functional units and having bound thereto said plurality of groups displaying chemiluminescence (a) and said plurality of haptens (c).

9. Labelled hapten conjugate according to claim 8, wherein the linkage group (b) is a peptide, a glycoprotein, a glycolipid or a carbohydrate.

10. Labelled hapten conjugate according to claim 9, wherein the molar ratio of the linkage group (b) to the group (a) capable of luminescence to the hapten (c) is at least 1:10:10.

11. The test kit of claim 1 wherein said linkage group (b) is transferrin or thyroglobulin.

12. The chemiluminescence-labeled hapten conjugate of claim 8 wherein said linkage group (b) is transferrin or thyroglobulin.

* * * * *